United States Patent [19]

Schulte-Elte et al.

[11] Patent Number: 4,717,771
[45] Date of Patent: Jan. 5, 1988

[54] UNSATURATED ALIPHATIC KETONE [AND USE OF SAME AS PERFUMING INGREDIENT]

[75] Inventors: Karl-Heinrich Schulte-Elte, Onex; Dietrich Kastner, Givrins, both of Switzerland

[73] Assignee: Firmenich SA, Geneva, Switzerland

[21] Appl. No.: 784,126

[22] Filed: Oct. 4, 1985

[30] Foreign Application Priority Data

Oct. 15, 1984 [CH] Switzerland ............... 4926/84

[51] Int. Cl.⁴ .......................................... C07D 303/32
[52] U.S. Cl. ................................... 549/548; 549/524; 549/525; 549/531
[58] Field of Search ............... 549/524, 525, 531, 548

[56] References Cited

U.S. PATENT DOCUMENTS

| | | | |
|---|---|---|---|
| 3,501,503 | 3/1970 | Cragoe et al. | 549/548 |
| 3,928,456 | 12/1975 | Kovats et al. | 260/586 R |
| 3,931,326 | 1/1976 | Kovats et al. | 549/548 X |
| 3,975,310 | 8/1976 | Kovats et al. | 252/522 |
| 4,187,863 | 2/1980 | Kovats et al. | 426/538 |
| 4,226,892 | 10/1980 | Kovats et al. | 426/538 |
| 4,609,491 | 9/1986 | Schenk | 252/522 |

FOREIGN PATENT DOCUMENTS

| | | |
|---|---|---|
| 0096243 | 12/1983 | European Pat. Off. . |
| 520479 | 5/1972 | Switzerland . |
| 536834 | 6/1973 | Switzerland . |
| 1240309 | 7/1971 | United Kingdom . |
| 1240310 | 7/1971 | United Kingdom . |

OTHER PUBLICATIONS

Caubore et al., Chemical Abstracts, vol. 78 (1973) 15595g.

Primary Examiner—Richard L. Raymond
Attorney, Agent, or Firm—Pennie & Edmonds

[57] ABSTRACT

2,3-Epoxy-1-(2,6,6-trimethyl-2-cyclohexen-1-yl)-1-butanone, an epoxy ketone of formula

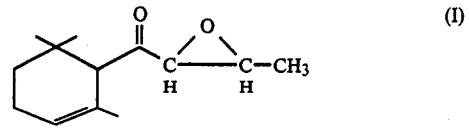

(I)

possesses useful fragrance characters and, consequently, it can be used advantageously in the manufacture of perfume, perfume bases and perfumed products. It develops a flowery and fruity odor.

1 Claim, No Drawings

UNSATURATED ALIPHATIC KETONE [AND USE OF SAME AS PERFUMING INGREDIENT]

BRIEF SUMMARY OF THE INVENTION

The invention provides a novel epoxy ketone, viz. 2,3-epoxy-1-(2,6,6-trimethyl-2-cyclohexen-1-yl)-1-butanone, a compound of formula

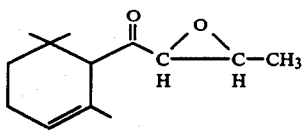 (I)

The invention provides further a perfume, a perfume base and a perfumed consumable material characterized in having added therein an odor modifying amount of 2,3-epoxy-1-(2,6,6-trimethyl-2-cyclohexen-1-yl)-1-butanone.

The invention provides also a method to confer or enhance the fruity, flowery odor of perfume, perfume bases and consumable materials which method comprises adding thereto an odor modifying amount of 2,3-epoxy-1-(2,6,6-trimethyl-2-cyclohexen-1-yl)-1-butanone.

BACKGROUND OF THE INVENTION

A variety of compounds, whose molecular structure is analogous to that of compound (I) of the instant invention, are known in the art. They belong to the class of chemicals which present an affinity with damascones and β-damascenones and since their discovery (see Swiss Pat. No. 520,479), the growing interest raised by this type of compounds has directed much of the industrial effort. Very numerous are indeed their applications, both in the flavour and the fragrance area.

Among the cited known compounds, one may cite the epoxides of formula

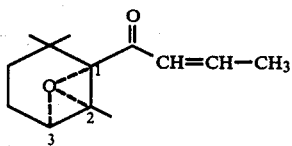

wherein the oxygen is bound to the carbon atoms at positions 1 and 2 or 2 and 3 of the cyclohexanic ring (see Swiss Pat. No. 536,834), which compounds are used as intermediates in a process for the preparation of β-damascenone. U.S. Pat. No. 3,931,326 mentioned also their organoleptic properties (see namely Example 40, column 53) without however describing their specific characters.

THE INVENTION

We have discovered that epoxy-ketone of formule (I) possesses useful fragrance properties and that consequently it can find an advantageous utilization in various applications, both in alcoholic and functional perfumery. It is primarily in this latter area of use that compound (I) finds its major interest. We have discovered in fact that the compound of the invention can be used to confer or enhance the odor of a variety of consumable materials, particularly of soaps, solid and liquid cationic, anionic, non ionic or zwitterionic detergents or fabric softeners. In typically aggressive media, such as for example in detergents, the compound of the invention has resulted particularly stable; it possesses moreover a good substantivity on fabrics of both natural and artificial fibers and its olfactive performance is homogeneous over the time. Besides, the epoxy-ketone of the invention has appeared as perfectly innocuous to man and to the environment and its utilization can be envisaged therefore in a high grade of concentrations.

From the point of view of its odor properties, the compound of the invention differs from the structurally analogous prior known compounds of the art, on account of its flowery, fuity note, in which, however, the typical apple character of α-damascone is absent, or at least present in a much lesser degree. Compound (I) does not possess the slightly camphory character typical of certain quality of α-damascone and, on the contrary, it develops a faint earthy, green and natural note.

When compared with the prior known compound of formula

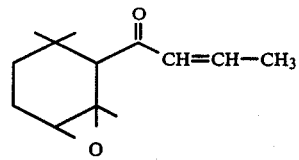

2,3-epoxy-1-(2,6,6-trimethyl-2-cyclohexen-1-yl)-1-butanone develops a very different odor of much nobler character. The above cited isomer possesses in fact a winery, terpenic, camphory or musty smell. Their domain of application is therefore quite distinct.

This observation confirms, if necessary, the character of uncertainty that surrounds olfactive perception. Experience shows in fact that a modification of the atomic arrangement in a given molecule brings about modifications, often to a large extent, of the fragrance properties of the product in question, without any apparent rational reason.

2,3-Epoxy-1-(2,6,6-trimethyl-2-cyclohexen-1-yl)-1-butanone can be utilized according to the invention in a wide range of proportions. Its power can be considered as moderate, thus concentrations of the order of 5, 10 or even 20% or more by weight, based on the total weight of the composition or consumable material into which it is added are sometimes necessary.

It is apparent to those skilled in the art that these values of concentrations depend on the nature of the materials it is desired to perfume or of the coingredients present in a given composition and, of course, of the specific effects one desires to achieve.

Typically, for instance in the perfuming of soaps and detergents, concentrations of the order of 1 or 2% by weight have been found as satisfactory.

The compound of the invention can be employed by directly adding it to the composition or consumable material it is desired to perfume or, more conveniently, in admixture with other current perfume coingredients. As an example of permissible current coingredients of natural or synthetic origin, one may cite those compounds described in European patent application published under No. 0096243.

As said above, 2,3-epoxy-1-(2,6,6-trimethyl-2-cyclohexen-1-yl)-1-butanone is a novel chemical entity. It can be prepared according to a process which consists in the epoxydation of α-damascone by means of an epoxydizing agent in a basic medium. Suitable epoxydizing agents include hydrogen peroxide and alkali metal perborate. Hydrogen peroxide is preferred and the reaction is carried out in the presence of sodium or potassium hydroxide in an aqueous or an aqueous-alcoholic solution.

It is apparent that the epoxy-ketone of the invention, as depicted by formula (I), is characterized by the existence of several centers of asymmetry in its molecule. It has to be understood that the given formula defines any of the possible epimer or enantiomer. For practical and economical reasons, epoxy-ketone (I) will be utilized in the isomeric form in which the compound occurs when prepared by the epoxydation process described above.

The invention is illustrated in a more detailed manner by the following examples wherein the temperatures are indicated in degrees centigrade and the abbreviations have the meaning common in the art.

EXAMPLE 1

Preparation of 2,3-epoxy-1-(2,6,6-trimethyl-2-cyclohexen-1-yl)-1-butanone

To a solution of 3.9 g of α-damascone, 4.6 g of 30% solution of $H_2O_2$ and 200 ml of methanol, there were added 1.2 ml of 6N NaOH while the reaction vessel was cooled by an external ice bath, whereupon the obtained mixture was kept at room temperature for 48 h and diluted then with 200 ml of water. The reaction mixture was then extracted with ether and the obtained organic extracts were dried and evaporated to give 4.1 g of a residue which upon distillation in a bulb-to-bulb apparatus yielded 3.8 g (yield 90%) of the desired epoxy-ketone under the form of a diastereoisomeric mixture.

$n_D = 1.4848$; $d^{20} = 0.9928$.

IR: 1700, 815 cm$^{-1}$.

NMR (60 MHz): 0.86; 0.89; 0.91 (several singlets, 6H); 1.36 and 1.38 (2×d, J=5.5 Hz, 3H); 2.75 and 3.02 (several m, 2H); 5.45 (m, 2H) δppm.

MS: M$^+$=208(1); m/e: 193(2), 175(1), 163(0,5), 152(7), 135(3), 123(100), 107(68), 95(21), 81(68), 67(17), 55(15), 41(35), 29(20).

EXAMPLE 2

Perfume composition for soaps

A perfume composition for soaps was prepared by mixing the following ingredients (parts by weight):

| Geranylacetone | 200 |
|---|---|
| Benzyl acetate | 140 |
| Phenylethyl alcohol | 100 |
| Ethyl acetoacetate | 100 |
| Diethylacetal of α-amylcinnamic ald. | 80 |
| Trimethylcyclohexenecarbaldehyde 10%* | 60 |
| Verdox IFF[1] | 40 |
| Musk DTI[2][3] | 40 |
| Hedione[3][4] | 40 |
| Citronollol | 20 |
| α-Hexylcinnamic ald. | 10 |
| Epoxy-ketone of Example 1 | 170 |
| | 1000 |

*in diethyl phthalate
[1] 2-tert-butyl-1-cyclohexyl acetate
[2] 1,1-dimethyl-4-acetyl-6-tert-butylindane
[3] origin: Firmenich SA, Geneva
[4] methyl dihydrojasmonate The fruity character of the base composition was pleasantly modified by the addition of the epoxy-ketone of Example 1. By comparison, when adding to the base composition α-damascone in the same proportion instead of the said epoxy-ketone, a novel composition resulted whose fruity character however was too pronounced; the harmony of the fragrance was thus distorted.

EXAMPLE 3

Perfume composition for a hair-set solution

A perfume composition destined to perfume a solution for hair-set was prepared by mixing the following ingredients (parts by weight):

| Benzyl salicylate | 150 |
|---|---|
| Bicyclopentadienyl acetate | 80 |
| Geraniol | 80 |
| Synth. rose Oil | 60 |
| 3,5,5-Trimethylhexyl acetate | 50 |
| Cyclopidene[1][2] 10%* | 50 |
| Synth. jasmin oil | 40 |
| Lilial[3] | 40 |
| Cinnamic alcohol | 40 |
| Synth. galbanum resinold | 30 |
| Lyral[4] | 30 |
| Cyclohexylethyl acetate | 30 |
| α-Isomethylionone | 30 |
| Dimethylbenzylcarbinol | 30 |
| Mayol[5][2] | 20 |
| Synth. lily-of-the-valley | 20 |
| Benzophenone | 20 |
| Citralva[6] 10%* | 20 |
| Methyl cyclogeraniate 10%* | 20 |
| Galaxolide[4] | 20 |
| Patchouli oil 10%* | 20 |
| Coumarin 10%* | 20 |
| Epoxy-ketone of Example 1 | 100 |
| | 1000 |

*in diethyl phthalate
[1] cyclopentylidene acetate
[2] origin: Firmenich SA, Geneva
[3] origin: L. Givaudan, Vernier-Geneva
[4] origin: IFF
[5] 4-isopropyl-cyclohexyl-methanol
[6] geranonitrile The addition of the epoxy-ketone of Example 1 confers to the base brilliance and harmony to the fruity odor note.

EXAMPLE 4

Two powder detergent bases were prepared by mixing the following ingredients (parts by weight):

| | Composition | Composition with sodium perborate |
|---|---|---|
| Sodium linear alkyl-benzenesulphonate (chain length: $C_{11-5}$) | 8.0 | 6.4 |
| Ethoxylated tallow alcohol (14EO) | 2.9 | 2.3 |
| Sodium soap (chain length: $C_{12-16}$ 13-26%; $C_{18-22}$ 74-87%) | 3.5 | 2.8 |
| | 3.5 | 2.8 |
| Sodium triphosphate | 43.8 | 35.0 |
| Sodium silicate | 7.5 | 6.0 |
| Magnesium silicate | 1.9 | 1.5 |
| Carboxymethylcellulose | 1.2 | 1.0 |
| Sodium EDTA | 0.2 | 0.2 |
| Sodium sulphate | 21.2 | 17.0 |
| Water | 9.8 | 7.8 |
| Sodium perborate | — | 20.0 |
| | 100.0 | 100.0 |

By adding to a sample of each of the above detergent bases 1% of the product of Example 1, there were obtained two novel compositions having a powerful and elegant fruity note.

EXAMPLE 5

A fabric softener base was prepared by mixing the following ingredients (parts by weight):

| Ingredient | Parts by weight | Origin |
|---|---|---|
| Praepagen WK | 10.0 | Hoechst |
| Emulgator O120 | 0.5 | Zschimmer & Schwarz |
| Polyglycol 400 | 2.0 | Hoechst |
| Distilled water | 84.4 | |
| Dye: | | |
| Brilliant Blau R 28032 in H$_2$O sol. at 0.5% | 0.1 | Siegle |
| Sodium chloride in H$_2$O sol. at 10% | 0.7 | |
| Poromycen F 10 | 0.1 | Kraft |
| Isopropylic alcohol C+ | 2.0 | Shell |
| | 99.8 | |

The addition of the compound of Example 1 to the base at a concentration of 1% by weight confers to it an agreeable fuity fragrance.

EXAMPLE 6

By using the product of Example 1 at the concentration indicated, the following consumable materials were perfumed:

| | |
|---|---|
| Lotion | 5.0% |
| Day cream | 0.4% |
| Night cream | 0.4% |
| Shampoos | 0.5% |
| Deodorant (aerosol) | 1.2% |
| Hair lacquer | 0.3% |
| Soap[1] | 0.5% |
| Talc | 0.5% |
| Chlorinated dish washing detergent powder | 0.2% |

[1]Type: LUX, Unilever Ltd.

The product thus perfumed presented an agreeable fuity scent. The odor was stable as resulted by storage of the materials over a period of 1 month at 40°.

What we claim is:

1. An epoxy-ketone of formula

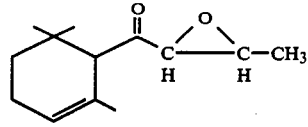

(I)